US00PP18816P3

(12) United States Plant Patent
Bradford

(10) Patent No.: US PP18,816 P3
(45) Date of Patent: May 13, 2008

(54) PEACH TREE NAMED 'NEPTUNE I'

(50) Latin Name: *Prunus persica*
Varietal Denomination: NEPTUNE I

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/453,792

(22) Filed: Jun. 16, 2006

(65) Prior Publication Data

US 2007/0294794 P1 Dec. 20, 2007

(51) Int. Cl.
*A01H 5/00* (2006.01)

(52) U.S. Cl. ..... Plt./196
(58) Field of Classification Search ..... Plt./196
See application file for complete search history.

(56) References Cited

U.S. PATENT DOCUMENTS

PP5,123 P * 10/1983 Bailey et al.
PP7,193 P * 3/1990 Bradford et al.

* cited by examiner

*Primary Examiner*—Kent Bell

(57) ABSTRACT

The present invention relates to a peach tree, *Prunus persica,* and more particularly to a new and distinct variety characterized by a large size, vigorous, hardy, self-fertile, productive and regular bearing tree. The fruit matures under the ecological conditions described in the first half of July, with first picking on Jul. 8, 2005. The fruit is uniformly medium in size, sub-acid and sweet in flavor, very oblate in shape, freestone in type, firm in texture, white in flesh color, and mostly red in skin color. The variety was developed as a first generation cross using 'Red Glen' (U.S. Plant Pat. No. 7,193) yellow flesh nectarine as the selected seed parent and an unnamed flat peach as the selected pollen parent.

1 Drawing Sheet

Botanical classification: *Prunus persica.*
Variety denomination: 'Neptune I'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'Neptune I'. The present variety was hybridized by me in 1999, grown as a seedling on its own root in my greenhouse, and transplanted to a cultivated area of my experimental orchard at Bradford Farms near Le Grand, Calif. in Merced County (San Joaquin Valley).

The variety was developed as a first generation cross using 'Red Glen' (U.S. Plant Pat. No. 7,193) yellow flesh nectarine as the selected seed parent and an unnamed peach (unpatented) as the selected pollen parent. A single tree from the stated cross was selected as the claimed variety. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is very distinguished from its selected seed parent, 'Red Glen' (U.S. Plant Pat. No. 7,193) nectarine, by producing fruit that is peach instead of nectarine, oblate instead of globose in shape, white instead of yellow in flesh color, sub-acidic instead of acidic in flavor, and freestone instead of clingstone.

The present variety is most similar to 'Saturn' (U.S. Plant Pat. No. 5,123) peach by producing fruit that is white in flesh color, very oblate in shape, and freestone in type, but is distinguished therefrom and an improvement thereon by having a much lower chilling requirement and by producing fruit that has a higher percentage of red color, firmer in texture, and ripens about 10 days later in the Central Valley of California.

SUMMARY OF VARIETY

In summary, the present variety is characterized by a large size, vigorous, hardy, self-fertile, productive and regular bearing tree. The fruit matures under the ecological conditions described in the first half of July, with first picking on Jul. 8, 2005. The fruit is uniformly medium in size, sub-acid and sweet in flavor, very oblate in shape, freestone in type, firm in texture, white in flesh color, and mostly red in skin color.

DRAWING

The accompanying photograph exhibits two whole fruits positioned to display the characteristics of the skin color and form, one fruit divided along the suture plane to reveal the flesh and stone, one fruit divided transverse to the suture plane, typical leaves, and an inset depicting an array of buds, blossoms, and flower parts.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jul. 10, 2005, on the original tree during its sixth growing season. All major color code designations are by reference to the Inter-Society Color Council, National Bureau of Standards. Common color names are also used occasionally.

Tree

Size: Large, reaching a height of 14' [4.27 m.] and a spread of 9' [2.74 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 575 hours.

Trunk:

*Size.*—Medium, with a maximum diameter of 3¾" [95.3 mm.] after the sixth growing season.

*Texture.*—Rough to somewhat shaggy.

*Bark color.*—Deep brown [56. deep Br].

*Lenticels.*—Average Number Per Square Inch: 14. Color: Brilliant orange yellow [67. brill.OY]. Size: 3/16" [4.8 mm.] to 7/16" [11.1 mm.]. Shape: Eye-shaped to elongated.

Branches:

*Size.*—Diameter of limb is 2½" [63.5 mm.] measured 12" from the crotch, 1⅝" [41.3 mm.] measured 12" above first fork.

*Texture.*—Smooth on first year wood, increasing roughness with age.

*Color.*—1st Year Wood Topside: Grayish red [19. gy.R]. 1st Year Wood Underside: Vivid yellow green [115. v.YG]. Older Wood: Deep yellowish brown [75. deep yBr].

*Lenticels.*—Number Per Square Inch: More than 50. Color: Moderate orange yellow [71. m.OY]. Typical size: 1/32" [0.4 mm.] to ⅛" [3.2 mm.]. Shape: Eye-shaped to elongated.

Leaves:

*Size.*—Medium. Average Length: 5½" [140 mm.]. Average width: 1⅝" [41 mm.].

*Arrangement.*—Alternate.

*Thickness.*—Medium.

*Form.*—Elliptical.

*Apex.*—Acuminate.

*Base.*—Obtuse, with an average base angle of 100 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined, Light yellow green [119.l.YG] in color.

*Petiole.*—Average Length: 7/16" [11.1 mm.]. Average Thickness: 1/16" [1.6 mm.]. Color: Strong yellow green [117. s.YG].

*Stipules.*—Number: Up to 2 per leaf, usually 6 per growing tip. Average Length: ⅜" [9.5 mm.]. Color: Brilliant yellow green [116. brill.YG] becoming Moderate reddish brown [43. m.rBr] with age.

*Glands.*—Number: 2 to 6. Position: Oppositely positioned with two on the petiole and the rest on base of leaf blade. Size: Small. Form: Reniform. Color: Brilliant yellow green [116. brill.YG] when young becoming Dark reddish brown [44. d.rBr] in centers with age.

*Leaf buds.*—Small, pointed to conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Moderate purplish red [258. m.p.R].

Flowers: Perfect, complete, perigynous, usually a single pistil, typically thirty or more stamens, five sepals and petal locations alternately positioned.

*Type.*—Showy, large.

*Average flower diameter.*—1 13/16" [46.0 mm.].

*Number of petals.*—Usually five, with very few double blossoms.

*Petal shape.*—Circular to oval.

*Petal margin.*—Entire, wavy.

*Average petal diameter.*—11/16" [17.5 mm.].

*Average petal length.*—¾" [19.1 mm.].

*Petal apex.*—Rounded.

*Petal base.*—Somewhat cuneate to rounded.

*Petal color.*—Pale pink [7. p.Pk] toward the apex, Moderate purplish pink [250. m.pPk] toward the base on both sides.

*Anther color.*—Dark red [16. d.R] over Light Yellow [86. l.Y] centers at bloom onset.

*Stigma color.*—Light greenish yellow [101. l.gY].

*Sepal color.*—Dark purplish red [259. d.pR] on the outer surface.

*Sepal length.*—¼" [6.4 mm.].

*Sepal width.*—7/32" [5.6 mm.].

*Sepal apex.*—Rounded to elliptical to match the width and length.

*Sepal margin.*—Fairly smooth.

*Average pistil length.*—11/16" [17.5 mm.].

*Average stamen length.*—⅝" [15.9 mm.].

*Fragrance.*—Moderate.

*Blooming period.*—Medium compared with other varieties.

*Onset of bloom.*—One percent on Feb. 19, 2005.

*Date of full bloom.*—Feb. 28, 2005.

*Duration of bloom.*—One to two weeks, dependent on ambient temperature.

*Number per cluster.*—1 to 3 with single flowers most common.

FRUIT

Maturity when described: Firm ripe, Jul. 10, 2005.

Date of first picking: Jul. 8, 2005.

Date of last picking: Jul. 16, 2005.
Size: Uniform, medium.
*Average diameter axially.*—1⅜" [35 mm.] to 1½" [38.1 mm].
*Average diameter across suture plane.*—3" [76.2 mm.].
*Typical weight.*—4.4 ounces [124 grams].
Form: Uniform, symmetrical, oblate with axial compression.
*Longitudinal section form.*—Round to circular.
*Transverse section through diameter.*—Oblate, shaped like a peanut or a footprint.
Suture: A very distinguishable line with stitching appearing in the bottom of a fairly sharp groove that reaches from the stem to the apex, discontinuing with a marked depression at the pistil point.
Ventral surface: Rounded, lipped on the sides but not toward the apex or base.
Lips: Slightly unequal.
Cavity: Flaring, elongated in the suture plane, suture showing on both sides, Greenish white [153. g.White] stem markings typical.
*Depth.*—½" [12.7 mm.].
*Breadth.*—1⅜" [34.9 mm.].
Base: Cuneate when viewed along the suture, very truncate when viewed transversely to the suture.
Apex: Very truncate, flaring from the pistil point.
Pistil point: Negligible in length, buried within a cavity 1¼" [31.8 mm.] across and ⅜" [9.5 mm.] deep.
Stem: Small.
*Average length.*—¼" [6.4 mm.], with a small flange attached tightly to skin.
*Average width.*—⅛" [3.2 mm.].
Skin:
*Thickness.*—Medium, tough.
*Texture.*—Pubescent.
*Tenacity.*—Tenacious to flesh when shipping ripe becoming more free with increased maturity. Skin can be detached around the stem during the picking process, especially if fruit is overripe.
*Astringency.*—Nonastringent.
*Tendency to crack.*—A minor amount of apex cracking observed in dry season.
*Color.*—Dark red [16. d.R] over a Dark yellowish pink [30. d.yPk] background with very little freckling.
Down: Very short in length, does not roll up when rubbed.
Flesh:
*Color.*—Greenish white [153. g.White] with Deep red [13. deep R] flecking and bleeding, especially near the stone.
*Surface of pit cavity.*—Covered with Strong pink [2. s.Pk] fibers, with some Yellowish white [92. yWhite] callouses present.
*Amygdalin.*—Moderate.
*Juice.*—Abundant, rich.
*Texture.*—Firm, crisp.
*Fibers.*—Abundant, fine.
*Ripens.*—Somewhat earliest at the apex.
*Flavor.*—Mild, sweet, sub-acid, typically 15 to 19 brix, depending upon maturity.
*Aroma.*—Slight.
*Eating quality.*—Very good.

STONE

Type: Freestone.
Form: Elliptical, oblate.
Hilum: Narrow, oblong.
Base: Straight, truncate.
Apex: Truncate.
Sides: Equal.
Surface: Pitted throughout, no furrows except along the dorsal and ventral edges.
Ridges: Very few.
External color: Deep brown [56. deep Br].
Internal cavity color: Deep yellowish brown [75. deep yBr].
Average pit wall thickness: 1/16" [1.6 mm.] at the apex, ⅛" [3.2 mm.] at the base, and 3/16" [4.8 mm.] on the sides.
Average width: 13/16" [20.6 mm.].
Average length: 9/16" [14.3 mm.].
Average breadth: 13/16" [20.6 mm.].
Tendency to split: None observed.
Kernel:
*Form.*—Elliptical to oblate.
*Pellicle color.*—Grayish yellowish brown [80. gy.y.Br].
*Skin color.*—Pale yellow [89. p.Y] when freshly removed.
*Vein color.*—None.
*Taste.*—Bitter.
*Viable.*—Yes.
*Average width.*—⅜" [9.5 mm.].
*Average length.*—5/16" [7.9 mm.].
*Amygdalin.*—Abundant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Saturn' (U.S. Plant Pat. No. 5,123) peach by producing fruit that is white in flesh color, very oblate in shape, and freestone in type, but is distinguished therefrom and an improvement thereon by having a much lower chilling requirement and by producing fruit that has a higher percentage of red color, firmer in texture, and ripens about 10 days later in the Central Valley of California.

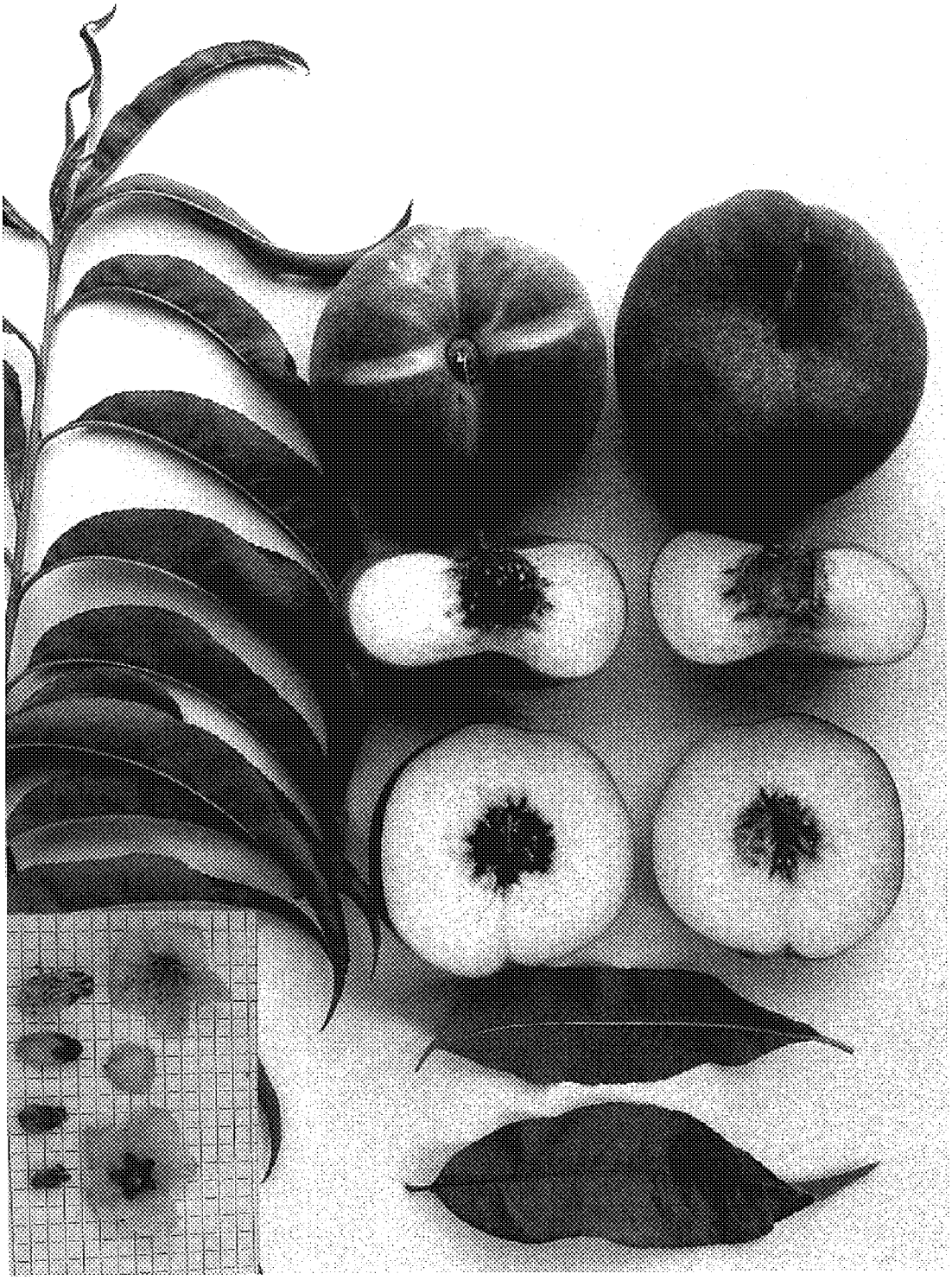

* * * * *